US008834558B2

(12) United States Patent
Nissl (10) Patent No.: US 8,834,558 B2
(45) Date of Patent: Sep. 16, 2014

(54) ESOPHAGEAL STENT AND ASSOCIATED METHOD (75) Inventor: Thomas Nissl, Winsen/Luhe (DE)

(73) Assignee: Merit Medical Systems, Inc., South Jordan, UT (US)

( * ) Notice: Subject to any disclaimer, the term of this patent is extended or adjusted under 35 U.S.C. 154(b) by 1217 days.

(21) Appl. No.: 11/410,426

(22) Filed: Apr. 25, 2006

(65) Prior Publication Data

US 2006/0259113 A1  Nov. 16, 2006

(30) Foreign Application Priority Data

Apr. 26, 2005 (DE) .......................... 10 2005 019 649

(51) Int. Cl.
*A61F 2/06* (2013.01)
*A61F 2/04* (2013.01)

(52) U.S. Cl.
CPC ............. *A61F 2/04* (2013.01); *A61F 2002/044* (2013.01); *A61F 2250/0029* (2013.01)
USPC .......................................... 623/1.3; 623/23.7

(58) Field of Classification Search
CPC ................ A61F 2/04; A61F 2002/043; A61F 2002/044; A61F 2002/045; A61F 2002/046; A61F 2/06; A61F 2/82; A61F 2250/0029
USPC .................. 623/1.23, 23.65, 23.7, 1.15–1.16, 623/1.28–1.31, 23.64–23.71; 604/8–9
See application file for complete search history.

(56) References Cited

U.S. PATENT DOCUMENTS

| 3,044,497 | A | | 7/1962 | Paul Rebut |
| 4,164,045 | A | * | 8/1979 | Bokros et al. ................. 623/1.28 |
| 4,313,231 | A | * | 2/1982 | Koyamada ................... 623/1.32 |
| 5,129,910 | A | | 7/1992 | Phan et al. |
| 5,282,847 | A | * | 2/1994 | Trescony et al. ............. 623/1.29 |
| 5,330,500 | A | | 7/1994 | Song |
| 5,476,506 | A | * | 12/1995 | Lunn ........................... 623/1.28 |

(Continued)

FOREIGN PATENT DOCUMENTS

| DE | 297 08 879 U1 | 7/1997 |
| DE | 691 26 428 T2 | 10/1997 |

(Continued)

OTHER PUBLICATIONS

*Ultraflex™Esophageal NG Stent System, Boston Scientific*; 2 pages, available at http://www.bostonscientific.com/med_specialty/deviceDetail.jsp?task=tskBasicDevice.jsp; Downloaded on May 19, 2005.

(Continued)

*Primary Examiner* — Andrew Iwamaye
(74) *Attorney, Agent, or Firm* — Stoel Rives LLP (57) ABSTRACT

A flexible stent and method for performing a stent within a lumen proximate to a target area is provided. The stent includes a tubular member having proximal and distal ends, where at least a portion of the tubular member is capable of being positioned proximate to the target area. The stent also includes a plurality of stabilization members defined circumferentially about at least a portion of the tubular member, wherein each stabilization member extends inwardly to define an inner diameter that is less than an inner diameter of the tubular member within the tubular member. As a result, the stabilization members are capable of reducing migration of the stent within the lumen and the incident of infolding of the tubular member.

24 Claims, 5 Drawing Sheets

(56) References Cited

U.S. PATENT DOCUMENTS

| | | | |
|---|---|---|---|
| 5,662,713 A * | 9/1997 | Andersen et al. | 128/898 |
| 5,723,003 A * | 3/1998 | Winston et al. | 623/1.13 |
| 5,866,217 A * | 2/1999 | Stenoien et al. | 623/1.44 |
| 5,876,448 A | 3/1999 | Thompson et al. | |
| 6,001,123 A * | 12/1999 | Lau | 623/1.12 |
| 6,017,365 A | 1/2000 | Von Oepen | |
| 6,106,548 A | 8/2000 | Roubin et al. | |
| 6,146,416 A | 11/2000 | Andersen et al. | |
| 6,176,873 B1 | 1/2001 | Ouchi | |
| 6,224,626 B1 | 5/2001 | Steinke | |
| 6,248,058 B1 | 6/2001 | Silverman et al. | |
| 6,273,909 B1 * | 8/2001 | Kugler et al. | 623/1.13 |
| 6,302,917 B1 | 10/2001 | Dua et al. | |
| 6,325,825 B1 | 12/2001 | Kula et al. | |
| 6,358,275 B1 * | 3/2002 | McIlroy et al. | 623/1.28 |
| 6,416,545 B1 | 7/2002 | Mikus et al. | |
| 6,425,915 B1 | 7/2002 | Khosravi et al. | |
| 6,475,232 B1 | 11/2002 | Babbs et al. | |
| 6,494,908 B1 | 12/2002 | Huxel et al. | |
| 6,505,654 B1 | 1/2003 | Andersen et al. | |
| 6,589,213 B2 | 7/2003 | Reydel | |
| 6,652,573 B2 | 11/2003 | Von Oepen | |
| 6,675,809 B2 | 1/2004 | Stack et al. | |
| 6,746,489 B2 | 6/2004 | Dua et al. | |
| 6,818,015 B2 | 11/2004 | Hankh et al. | |
| 6,911,041 B1 * | 6/2005 | Zscheeg | 623/1.15 |
| 7,060,092 B2 * | 6/2006 | Kuribayashi et al. | 623/1.29 |
| 7,575,591 B2 * | 8/2009 | Howat et al. | 623/1.13 |
| 2001/0027341 A1 * | 10/2001 | Gianotti | 623/1.22 |
| 2002/0062148 A1 * | 5/2002 | Hart | 623/1.15 |
| 2003/0024534 A1 * | 2/2003 | Silvestri et al. | 128/846 |
| 2003/0040803 A1 | 2/2003 | Rioux et al. | |
| 2003/0072868 A1 | 4/2003 | Harish et al. | |
| 2003/0130611 A1 | 7/2003 | Martin | |
| 2003/0139799 A1 * | 7/2003 | Ley et al. | 623/1.15 |
| 2003/0176831 A1 * | 9/2003 | Gellman et al. | 604/8 |
| 2003/0199989 A1 * | 10/2003 | Stack et al. | 623/23.65 |
| 2003/0212450 A1 | 11/2003 | Schlick | |
| 2004/0015228 A1 * | 1/2004 | Lombardi et al. | 623/1.18 |
| 2004/0049264 A1 * | 3/2004 | Sowinski et al. | 623/1.28 |
| 2004/0102833 A1 * | 5/2004 | Girton et al. | 623/1.11 |
| 2004/0102855 A1 * | 5/2004 | Shank | 623/23.68 |
| 2004/0182511 A1 * | 9/2004 | Rakos et al. | 156/287 |
| 2004/0193283 A1 | 9/2004 | Rioux et al. | |
| 2005/0010275 A1 | 1/2005 | Sahatjian et al. | |
| 2005/0033418 A1 * | 2/2005 | Banas et al. | 623/1.49 |
| 2005/0055039 A1 * | 3/2005 | Burnett et al. | 606/151 |
| 2005/0060023 A1 * | 3/2005 | Mitchell et al. | 623/1.15 |
| 2005/0075715 A1 | 4/2005 | Borges et al. | |
| 2005/0143805 A1 | 6/2005 | Hierlemann et al. | |
| 2006/0047334 A1 * | 3/2006 | Houston et al. | 623/1.1 |
| 2006/0106455 A1 * | 5/2006 | Furst et al. | 623/1.31 |
| 2006/0129232 A1 * | 6/2006 | Dicarlo et al. | 623/1.19 |
| 2008/0275541 A1 * | 11/2008 | Furst et al. | 623/1.31 |

FOREIGN PATENT DOCUMENTS

| | | | |
|---|---|---|---|
| DE | 197 54 747 A1 | 6/1999 | |
| DE | 199 49 334 A1 | 4/2001 | |
| DE | 693 33 161 T2 | 3/2004 | |
| EP | 0666066 | 8/1995 | |
| EP | 0 836 450 B1 | 4/1998 | |
| GB | 2 069 339 | 8/1981 | |
| GB | 2069339 A * | 8/1981 | A61M 25/00 |
| WO | WO-90/04982 A1 | 5/1990 | |
| WO | WO-94/12136 A1 | 6/1994 | |
| WO | WO-99/49810 A1 | 10/1999 | |
| WO | WO-01/58384 A1 | 8/2001 | |
| WO | WO-01/72239 A2 | 10/2001 | |
| WO | WO 01/89419 | 11/2001 | |
| WO | WO 02/069848 | 9/2002 | |
| WO | WO 2004/096097 A2 | 11/2004 | |
| WO | WO 2004/100827 | 11/2004 | |
| WO | WO-2005/011527 A1 | 2/2005 | |

OTHER PUBLICATIONS

*Polyflex® Esophageal Stent*, Boston Scientific, 2 pages, available at http://wwwbostonscientific.com/med_specialty/deviceDetail.jhtml?task=tskBasicDevice.jht; Downloaded on May 19, 2005. Examiner.

PCT Notification of Transmittal of the International Search Report and the Written Opinion of the International Searching Authority, or the Declaration, mailed Jul. 25, 2006 for PCT/US2006/015719 (Filed Apr. 25, 2006).

European Examination Report dated Mar. 25, 2014 for EP06751421.6.

\* cited by examiner

FIG. 5

ESOPHAGEAL STENT AND ASSOCIATED METHOD

CROSS-REFERENCE TO RELATED APPLICATIONS

The present application claims priority from German Application No. DE 10 2005 019 649, entitled "Wave Design," filed Apr. 26, 2005, the contents of which are incorporated herein by reference.

BACKGROUND OF THE INVENTION

1) Field of the Invention

The present invention relates to a stent and, in more particular, to a stent that is capable of being positioned within a lumen of the esophagus.

2) Description of Related Art

Stents are devices that are inserted into body lumina such as vessels or passages to keep the lumen open and prevent closure due to a stricture, external compression, or internal obstruction. In particular, stents are commonly used to keep blood vessels open in the coronary arteries, and they are frequently inserted into the ureters to maintain drainage from the kidneys, the bile duct for pancreatic cancer or cholangiocarcinoma, or the esophagus for strictures or cancer. Vascular as well as nonvascular stenting has evolved significantly; unfortunately, there remain significant limitations with respect to the effectiveness of the stents following implantation into a patient's esophagus.

Stenting of the esophagus has proven to be challenging. The esophagus is a muscular lumen that is about ten inches long and extends from the hypopharynx to the stomach. The esophageal lumen is subject to wavelike contractions known as peristalsis, which pushes food down through the esophagus to the stomach. The esophagus is subject to complications that may require stenting, surgical repair, or dilatation. For example, a benign or malignant tumor may form in the esophagus that may be unable to be surgically removed, necessitating stenting or further surgical repair to prevent the lumen from constricting further. Left untreated, the tumor may lead to dysphagia, resulting in difficulty in swallowing.

Conventional stents utilized for the esophagus have significant drawbacks. Because the esophagus is very soft and flexible compared to other lumina, preventing migration of the stent is problematic. In particular, the esophagus frequently changes size and position, which causes complications for typical stents. For instance, a stent having a constant diameter along its entire axial length will have a tendency to migrate as the esophagus expands. The stricture is narrower than the lumen located proximally and distally of the stricture, and the stent is longer than the length of the stricture such that the portions of the stent proximately and distally of the stricture do not help prevent the stent from migrating. Therefore, there is an increased possibility that the stent will migrate within the lumen.

Moreover, the esophageal lumen is muscular and its wavelike contractions generally travel from its proximal end to its distal end resulting from an impulse applied at one side of the lumen wall. Due to the actions of the lumen, flexible stents have been designed to mimic the movement of the lumen. However, flexible stents may be prone to infolding or kinking, effectively occluding one or both of the openings of the stent. Furthermore, providing more rigid stents increases the risk of damage to the lumen of the esophagus, such as by damaging the blood vessels lining the lumen. Rigid stents are also typically more prone to migration.

Thus, there is a need in the industry for an esophageal stent that is capable of conforming to a lumen and maintaining the opening through a stricture. In addition, there is a need for a esophageal stent that reduces migration and the possibility of obstruction of the stent openings.

BRIEF SUMMARY OF THE INVENTION

The invention addresses the above needs and achieves other advantages by providing a stent for a lumen of the esophagus. The stent includes a tubular member and stabilization members defined in the tubular member. The stabilization members are configured to reduce migration and infolding of the stent during peristalsis. Accordingly, the stent is capable of not only maintaining or even expanding a target area within a lumen but also mimicking the size and movement of the lumen.

In one embodiment of the present invention, a flexible stent for positioning within a lumen proximate to a target area is provided. The stent includes a tubular member having proximal and distal ends, where at least a portion of the tubular member is capable of being positioned proximate to the target area. The stent also includes a plurality of stabilization members defined circumferentially about at least a portion of the tubular member, wherein each stabilization member extends inwardly to define an inner diameter that is less than an inner diameter of the tubular member within the tubular member. As a result, the stabilization members are capable of reducing migration of the stent within the lumen and the incidence of infolding of the tubular member.

In various aspects of the stent, at least one of the proximal and distal ends of the tubular member further includes an end portion. The end portion at the proximal end can be larger in diameter and/or shorter in length than the end portion at the distal end. In addition, at least one stabilization member may be at least partially defined in the end portion, and/or the end portion could be more flexible than at least a portion of the tubular member. The tubular member could include at least one anti-migration spar capable of engaging the lumen to help prevent migration. The tubular member may include an interstice geometry, and the stabilization members may be integrally defined in the interstice geometry. The stabilization members can be located substantially between the proximal and distal ends of the tubular member, and/or at least one stabilization member is capable of being positioned proximate to the target area.

In further aspects of the stent, each stabilization member could be a ring, where the rings are spaced apart from one another between the proximal and distal ends. A portion of the tubular member extending between respective rings may extend radially outward to define a convex cross section. Moreover, the stent may include a curved transition between the tubular member and each stabilization member. Each stabilization member could be a turn defined by a helical groove. Additionally, each of the stabilization members can be equidistantly spaced apart from one another, and/or can include at least a portion of a circular segment in cross section. Each of the stabilization members may curve inwardly to define a concave cross section within the tubular member. Furthermore, an outer diameter of each of the stabilization members could be less than the inner diameter of the tubular member, and/or a thickness of each of the stabilization members could be less than a thickness of the tubular member.

An additional aspect of the present invention provides a method for deploying a stent within a body lumen proximate to a target area. The method includes providing a stent comprising a tubular member and a plurality of stabilization members defined circumferentially about at least a portion of the tubular member, wherein each stabilization member extends inwardly to define an inner diameter that is less than an inner diameter of the tubular member within the tubular member. The method also includes compressing the stent to a diameter smaller than that of the lumen, and positioning the stent in a predetermined position within the lumen. The method further includes deploying the stent within the lumen such that the stent expands to conform to the target area.

Variations of the method include providing at least one stabilization member configured as a ring, or providing at least one stabilization member configured as a turn defined by a helical groove. Additionally, the method can include positioning at least one stabilization member proximate to the target area.

BRIEF DESCRIPTION OF THE SEVERAL VIEWS OF THE DRAWINGS

Having thus described the invention in general terms, reference will now be made to the accompanying drawings, which are not necessarily drawn to scale, and wherein:

DETAILED DESCRIPTION OF THE INVENTION

The present invention now will be described more fully hereinafter with reference to the accompanying drawings, in which some, but not all embodiments of the invention are shown. Indeed, this invention may be embodied in many different forms and should not be construed as limited to the embodiments set forth herein; rather, these embodiments are provided so that this disclosure will satisfy applicable legal requirements. Like numbers refer to like elements throughout.

Figure 1:
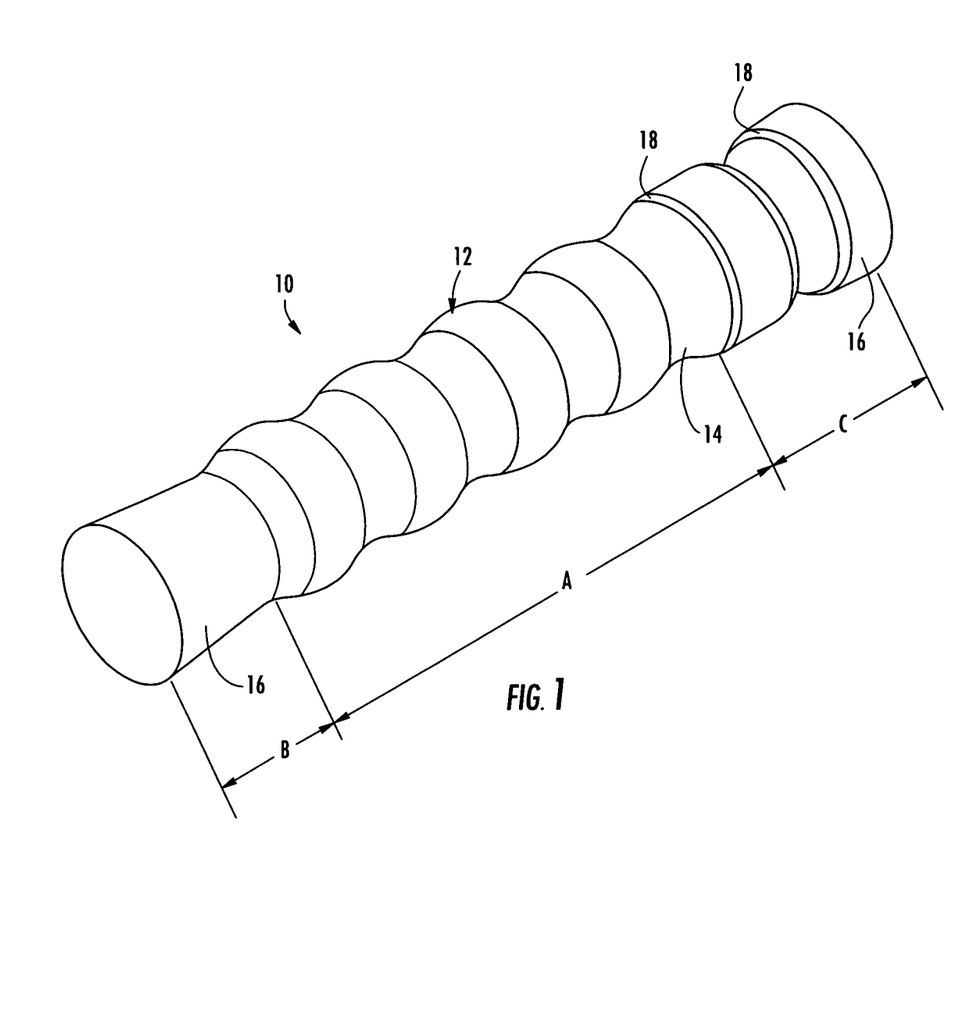
FIG. 1 is a perspective view of a stent according to one embodiment of the present invention.

With reference to FIG. 1, an esophageal stent 10 is shown. The stent 10 includes a tubular member 12 having a plurality of stabilization members 14 defined circumferentially therein. Generally, the stent 10 is positioned within the lumen adjacent to a target area, while the stabilization members 14 are configured to adapt to the muscular contractions of the esophagus thereby reducing migration of the stent 10 and the incidence of infolding of the tubular member 12.

Thus, the esophageal stent 10 is capable of being deployed proximate to a target area within a lumen of the esophagus. "Target area," as used herein, is not meant to limiting, as the target area, could be a stricture, lesion, tumor, fistulae, occlusion, or other complication where the lumen passageway has been significantly reduced or compromised. The term "stent" is also not meant to be limiting, as the stent could be any suitable implantable device capable of being deployed within a lumen and having stabilization members 14, as described herein. Moreover, although reference is made herein to an esophageal stent 10, it is understood that the stent is applicable to a wide range of stenting applications. For example, the stent 10 could be used for stenting lumina of the duodenum, vascular lumina, or lumina of the biliary tract.

The stent 10 may include an interstice geometry including a scaffolding of struts. The struts generally include a plurality of flexible interconnected legs and connectors. Thus, the stent 10 may include a series of legs arranged circumferentially about the stent, as well as arranged in a series of rows along the longitudinal axis of the stent, while a plurality of connectors are arranged parallel to the longitudinal axis of the stent to connect the rows together. However, the stent 10 could be a solid material with no interstice geometry if desired or indicated for a particular lumen.

Moreover, the stent 10 could comprise a grid or mesh structure. The grid structure is typically fabricated from a tube pre-formed with depressions and provided with cut-outs using a laser. The remaining grid structure includes webs with connections therebetween and having the flexibility and strength to impart a desired flexibility and strength. The strength of the stent can be modified by altering the web width and/or increasing or decreasing the cut-outs. A mesh structure is typically woven using suitable wires. The meshes or honeycombs can be modified locally as required with a view to adapting the level of flexibility and/or strength to specific requirements. Generally, greater strength will be provided in the stent neighboring the target area to be bridged, such as by using an increased web width or a higher mesh density, as well as more tightly spaced stabilization members 14, in the area of the stent proximate the target area.

The stent 10 is preferably formed from a material such as Ni, C, Co, Cu, Cr, H, Fe, Nb, O, SS, Ti and composites, alloys and combinations thereof (e.g., Nitinol), but could also be formed of polymeric materials. The material is generally formed into a tube from which the stent is etched or laser cut and is formed on a suitable shaping device to give the stent the desired external geometry. The stent 10 is typically formed of a memory material that facilitates flexibility of the stent region such that the stent may be deformed and return to its original shape. This flexibility allows the stent to be compressed radially for insertion into a stent delivery device, as discussed below, so as to self-expand when released into the lumen.

It should be pointed out that, unlike the use of differing shape memory materials to change portions of a stent 10, stents in accordance with the present invention can take on various characteristic combinations of interstice geometry by changing angles, segment lengths, and segment thicknesses during the cutting and forming stages of stent engineering or during post-formation processing and polishing steps. Moreover, by modifying the geometry of the connectors, additional functionality may be achieved. In the event the stent 10 is to be shaped to the dimensions of a particular lumen, optical photography and/or optical videography of the target lumen may be conducted prior to stent formation. The interstice geometry of the stent 10 then can be etched and formed in accordance with the requirements of that lumen and/or target area.

Furthermore, the stent 10 may be coated or covered along its entire length or over portions of the tubular member, such as with polyurethane or silicone, in alternative aspects of the present invention. In addition, the stent 10 could include a suture arranged about the proximal and/or distal ends of the tubular member 12 for repositioning or removing the stent. Spars, barbs, or the like may be incorporated into the geometry of the stent 10 at various locations, such as near the proximal and distal ends of the stent, in order to reduce migration following implantation within the lumen.

Various configurations of stents 10 could be incorporated and still be within the present scope of the invention as long as the configurations achieved are consistent with the geometry of the invention as described herein. An exemplary embodiment of the interstice geometry of a stent 10 of the present invention and methods of manufacturing the stent is disclosed in U.S. Patent Application Publication No. 20040127973, entitled "Removable Biliary Stent," which is assigned to the present assignee and is incorporated herein by reference. Thus, the interstice geometry of the stent 10 should not be limited to that described herein, as any number of configurations of interstice geometry could be employed with the present invention to achieve various degrees of rigidity and functionality.

Figure 2:
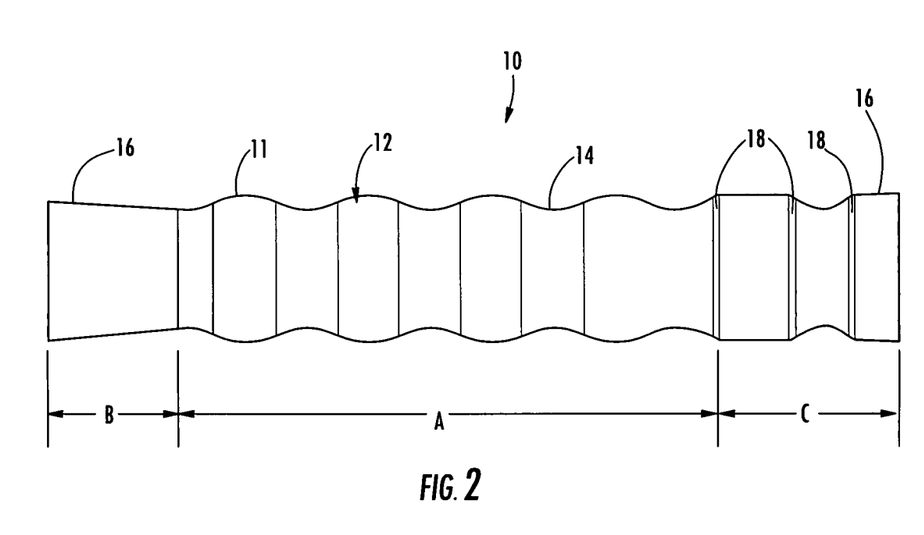
FIG. 2 is an elevation view of the stent shown in FIG. 1.

The stent 10 is generally tubular, having openings at the proximal and distal ends, but could also have different geometrical forms, such as a horseshoe-shaped cross section suitable for tracheal stents. As illustrated in FIGS. 1 and 2, the proximal and distal ends of the tubular member 12 include one or more end portions 16 (areas B and C). The diameter of the end portions 16 can be slightly larger than the diameter of the core area A of the tubular member 12 extending therebetween so as to receive the target area and anchor the stent relative to the target area. In particular, the end portion 16 in area B includes a slightly conical flared tube segment, which adjoins a "valley" and slightly flares out towards its end. The end portion 16 defined by area C includes an essentially cylindrical segment, which adjoins the core area A at the level of a "peak" and is itself provided with a stabilization member 14. The transitions of the depressions or "valleys" into the tubular member 12 are provided with an additional bevel 18 to eliminate sharp edges. The bevels 18 can generally be used rather than rounded edges.

The end portion 16 at the proximal end of the tubular member 12 may be shorter and slightly larger in diameter than the end portion at the distal end of the tubular member or vice versa. However, the end portions 16 can be various sizes and configurations depending on the particular lumen or target area being stented. For instance, the end portions 16 could be the same size and configuration if desired. Furthermore, the end portions 16 could also be more or less flexible or strong than the tubular member 12 extending therebetween such as by utilizing different materials, reinforced materials, or materials that have been modified by a particular treatment. In addition, the flexibility and/or strength of the end portions 16 could also be modified by leaving the end portions free from stabilization members 14.

FIG. 1 demonstrates that there are a plurality of stabilization members 14 extending circumferentially about the tubular member 12. Each of the stabilization members 14 is generally configured as a ring that defines a concave or smaller diameter portion than the larger diameter portions of the tubular member 12 extending between each stabilization member. The core area A is provided with a plurality of stabilization members 14 which, due to their rounded transitions with the tubular member 12, lead to a more or less waved pattern. The "peaks" of the tubular member 12 define the actual surface of the stent tube in the core area A. This design has the benefit that concentrated loads acting on the "peaks" in the area of the tubular member 12 are absorbed by the adjacent "valleys" of the stabilization members 14 and cannot lead to progressive infolding. This benefit is enhanced by the sphere-like surface shape; the core area A can also be described as a progression of sphere segments with rounded transitions. As such, the configuration of the stabilization members 14 defines an undulating or wavelike cross section substantially along the length of the tubular member 12, where each portion extending between respective stabilization members is generally convex in cross section. The radius of the stabilization members 14 and the radial portions 11 of the tubular member extending between each stabilization member are about the same such that there is a smooth transition between stabilization members. The stabilization members 14 are typically defined integrally within the tubular member 12 and are approximately the same distance apart from one another. Thus, the stabilization members 14 may include scaffolding, although the stabilization members could be a solid material having no interstice geometry if desired.

It is understood that the stabilization members 14 shown in FIG. 1 may be various sizes and configurations to achieve desired properties for a particular lumen or target area and still be within the scope of the present invention. For example, there may be at least one stabilization member 14 defined in the tubular member 12 and extending at least partially about the circumference of the tubular member, where each stabilization member may be defined at various locations. Generally, at least one stabilization member 14 is defined within the core area A of the tubular member 12. However, there could be one or more stabilization members 14 positioned at the proximal and/or distal ends of the tubular member 12, proximate to the target area, or substantially between the proximal and distal ends of the tubular member. Furthermore, the stabilization members 14 may not only be equidistantly spaced, but there may be a plurality of closely-spaced stabilization members 14 defined in the core area A of the tubular member 12 subject to loading (e.g., a target area), and widely-spaced stabilization members in other areas of the stent (areas B and C). Moreover, the stabilization members 14 can be various depths, cross sections, and widths, and may also extend at various angles about the tubular member. Each stabilization member 14 could also be a different size and configuration than another stabilization member defined in the same tubular member 12. For instance, the stabilization members 14 may be parallel or non-parallel to each other. In one embodiment of the present invention, the stent 10 is about 40-120 mm in length, and the stabilization members 14 are about 18-22 mm in diameter. The portions of the tubular member 12 extending between each stabilization member 14 can also be various configurations rather than a convex curvature. For instance, the portions of the tubular member 12 between the stabilization members 14 could be substantially cylindrical and have no curvature.

Figure 3:
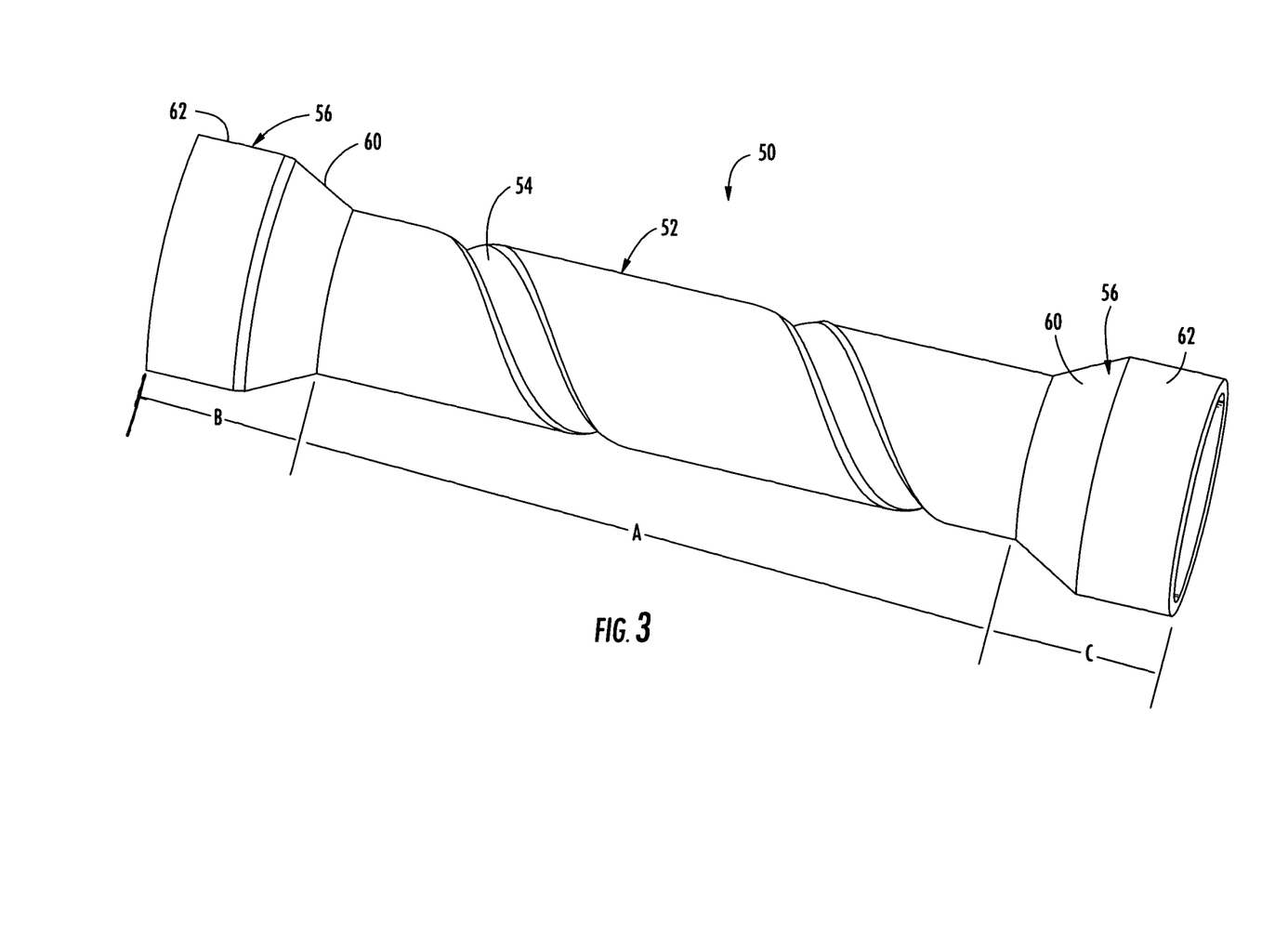
FIG. 3 is a perspective view of a stent according to another embodiment of the present invention.

Another embodiment of the present invention is depicted in FIG. 3. As described above with respect to FIG. 1, the stent 50 shown in FIG. 3 also includes a tubular member 52, stabilization members 54, and end portions 56 located at respective proximal and distal ends of the tubular member (areas B and C). However, comparison of FIGS. 1 and 3 demonstrates that the width and orientation of the stabilization members 54 may vary substantially. More specifically, the stabilization members 54 are defined as turns of a helical groove (i.e., each turn corresponds to a stabilization member when taken in cross section along the longitudinal axis of the tubular member 52). The helical groove includes a plurality of turns extending radially and longitudinally about the tubular member 52. In particular, FIG. 3 illustrates a single helical groove including two turns such that each turn defines a stabilization member 54. Each turn extends at an angle of about 60 degrees from the longitudinal axis of the tubular member 52. The end portions 56 generally include a conical section 60 adjacent to the core area A of the tubular member 52, while the most proximal and distal portions of the tubular member include generally cylindrical sections 62. The core area A is generally cylindrical in configuration.

As before, the stabilization member 54 may be various sizes and configurations depending on the particular characteristics of the stent 50 desired. For instance, there may be one or more helical grooves and/or turns for each helical groove.

Figure 4:
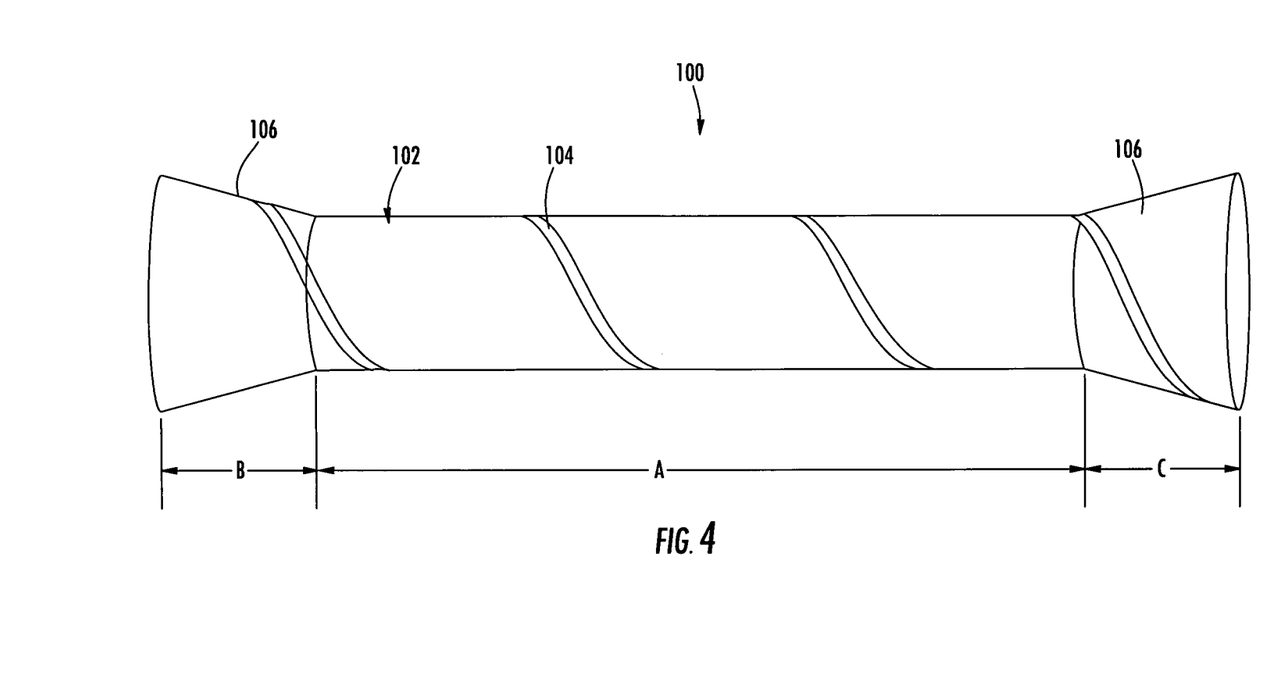
FIG. 4 is a perspective view of a stent according to another embodiment of the present invention.

In addition, the helical grooves may be defined at various depths and locations within the tubular member 52 and extend at different angles radially about the tubular member. For example, FIG. 4 demonstrates an additional embodiment of the present invention, wherein stabilization members 104 are defined by a single helical groove having four turns. FIG. 4 also shows that the stabilization members 104 may be defined in the end portions 106 of the tubular member 102. The helical groove of the stabilization members 104 is narrower than that of the stabilization members 54 shown in FIG. 3. Furthermore, the end portions 106 of the stent 100 depicted in FIG. 4 extend at an angle outwardly from the core area A of the tubular member 102.

Figure 5:
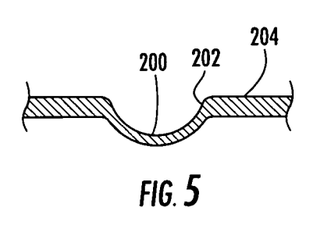
FIG. 5 is a cross-sectional view of a stabilization member according to one embodiment of the present invention.

FIG. 5 illustrates a cross-sectional view of a tubular member 204 with stabilization member 200 and rounded edges 202 according to one embodiment of the present invention. Rounded edges 202 provide a curved transition between the stabilization member 200 and the adjacent tubular member 204 in order to reduce tissue injury during deployment of the stent within the lumen. Various techniques may be utilized to form the stabilization members 204, such as mechanical imprinting or stamping. Due to the imprinting or stamping process employed to form the stabilization member 200, the material is typically subjected to stretching, which leads to a reduction in wall thickness in the area of the stabilization member. The stabilization member 204 is generally concave in configuration, such as a circular or semi-circular segment and can extend inwardly further than that shown in FIG. 5. Thus, the inner and outer diameters of each stabilization member 200 can be less than an inner diameter of the tubular member 204, as shown in FIG. 5. According to one aspect of the invention, the stabilization member 200 is typically a maximum of 10% of the diameter of the tubular member 204, preferably about 2-8%, and more preferably about 5%. However, the depth of the stabilization member 200 is dependent on the total diameter of the tubular member 204, the loads expected to occur within the lumen, and/or the material of the stent.

The esophageal stents 10, 50, and 100 may be deployed within a lumen of the esophagus using various techniques. For example, the esophageal stent is typically contracted to a smaller first diameter from a relaxed position. Once contracted, the esophageal stent is positioned within a delivery device, such as a catheter or tube that may be inserted within the lumen. The delivery device could be used to position and deploy the esophageal stent within the lumen. Examples of delivery devices suitable for implanting the esophageal stent are disclosed in U.S. patent application No. 60/680,556, entitled "Delivery Device with Shortened Inner Tube and Associated Method," and U.S. Patent Application Publication No. 20040193243, entitled "Medical Appliance Optical Delivery and Deployment Apparatus and Method," both of which are assigned to the present assignee and incorporated herein by reference. Similarly, techniques and devices known to those skilled in the art used to locate, contract, and/or remove the esophageal stent from the lumen may be employed with the present invention.

The esophageal stent is typically introduced orally with the delivery device, through the lumen, and proximate to a target area. The medial portion of the stent is positioned proximate to the target area such that when the esophageal stent is deployed from the catheter or tube, the stent, if formed from an expansible material, can expand to receive the target area and even expand the diameter of the target area. For example, the stent could open up the target area approximately 10-25 mm. Similarly, the end portions will be positioned proximally and distally of the target area and when deployed from the delivery device, will expand to contact the healthy tissue of the lumen and prevent migration. The stent is capable of dynamically expanding and retracting to closely mimic the motion of the lumen, which is beneficial for lumina such as the duodenum or esophagus where the lumen frequently changes size and position.

The present invention includes several advantages. The esophageal stent is capable of opening up a target area within a lumen to restore the patient's ability to swallow. The stabilization rings are configured such that forces applied through peristalsis is concentrated and distributed along the stabilization rings. Thus, the stabilization rings reduce the incidence of infolding of the stent by providing flexibility when external forces are applied to side of the stent. In particular, the stabilization members limit the progression of deformations in the longitudinal direction, as the stabilization members act as internal barriers, which adds stability to the stent without adversely affecting the stent's functionality. In addition, the stent decreases the incidence of occlusion of the stent openings without increasing the risk of damage to the wall of the esophageal lumen. Furthermore, the stabilization rings are configured to reduce migration of the stent within the lumen. Thus, the stabilization members may not only provide a configuration for mimicking the motion of the lumen, but the concave curvature of the stabilization members may also promote tissue ingrowth therein to aid in fixating the stent within the lumen.

Many modifications and other embodiments of the invention set forth herein will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A flexible stent for positioning within a lumen proximate to a target area, the stent comprising:
   a tubular member having proximal and distal ends, at least a portion of the tubular member comprising a self-expanding material, wherein at least a portion of the tubular member is configured to be positioned proximate to the target area, and wherein at least one of the proximal and distal ends of the tubular member comprises a flared end portion; and
   a plurality of stabilization members defined circumferentially about at least a portion of the tubular member, wherein each stabilization member extends inwardly within the tubular member to define an inner diameter that is less than an inner diameter of the tubular member, wherein the stabilization members are capable of reducing the incidence of infolding of the tubular member, wherein a wall thickness of each stabilization member is less than a wall thickness of the tubular member, and wherein the tubular member and stabilization members are integrally formed from a single piece of flexible material; and
   wherein the tubular member comprises a plurality of radial portions that are convex in longitudinal cross section, wherein each of said radial portions is shaped as a sphere segment so as to have a sphere-like surface shape such that at least a core area defined by the tubular member includes a progression of sphere segments, wherein the stabilization members are concave in longitudinal cross section, and wherein transitions between radial portions of the tubular member and the stabilization members are smooth.

2. The stent according to claim 1, wherein the proximal end comprises a flared end portion that is larger in diameter and shorter in length than an end portion at the distal end.

3. The stent according to claim 1, wherein at least one stabilization member is at least partially defined in the flared end portion.

4. The stent according to claim 1, wherein the flared end portion is more flexible than at least a portion of the tubular member extending therefrom.

5. The stent according to claim 1, wherein the tubular member comprises an interstice geometry.

6. The stent according to claim 5, wherein the stabilization members are integrally defined in the interstice geometry.

7. The stent according to claim 1, wherein each stabilization member comprises a ring, and wherein each ring is spaced apart from one another between the proximal and distal ends.

8. The stent according to claim 7, wherein a portion of the tubular member extending between respective rings extends radially outward to define a convex cross section.

9. The stent according to claim 1, further comprising a curved transition between the tubular member and each stabilization member.

10. The stent according to claim 1, wherein the stabilization members are located between the proximal and distal ends of the tubular member.

11. The stent according to claim 1, wherein at least one stabilization member is capable of being positioned proximate to the target area.

12. The stent according to claim 1, wherein each of the stabilization members are equidistantly spaced apart from one another.

13. The stent according to claim 1, wherein each of the stabilization members comprises at least a portion of a circular segment in cross section.

14. The stent according to claim 1, wherein an outer diameter of each of the stabilization members is less than the inner diameter of the tubular member.

15. The stent according to claim 1, wherein each of the stabilization members is mechanically imprinted or stamped in the tubular member.

16. A method for deploying a stent within a body lumen proximate to a target area, the method comprising:
providing a stent having a tubular member that comprises a centrally disposed core area that is cylindrical and an end portion that flares outwardly from an end of the core area such that each portion of the end portion defines a diameter that is greater than a maximum diameter defined by the core area, wherein the core area and the end portion are formed from a single piece of material, the stent further comprising a helical stabilization member defined about at least a portion of the tubular member such that the core area comprises at least a portion of the stabilization member and the end portion comprises at least a portion of the stabilization member, wherein the stabilization member is configured to limit the progression of deformations along the stent in a longitudinal direction, wherein the stabilization member comprises a groove that extends inwardly relative to the tubular member to define both an inner diameter and an outer diameter that are less than an inner diameter of the tubular member within the core area, wherein the stabilization member has a wall thickness that is less than a wall thickness of the tubular member, and wherein the stabilization member is bounded by transition regions between the tubular member and the stabilization member, the transition regions comprising a bevel;
constraining the stent to a diameter smaller than that of the lumen;
positioning the stent in a predetermined position within the lumen; and
deploying the stent within the lumen such that the stent self expands to conform to the target area.

17. The method according to claim 16, wherein at least a portion of the end portion is conical.

18. The method according to claim 16, wherein positioning comprises positioning at least one stabilization member proximate to the target area.

19. A flexible stent for positioning within a lumen proximate to a target area, the stent comprising:
a tubular member comprising a flexible self-expanding material such that at least a portion of the tubular member is configured to self-expand from a contracted position to an expanded position, wherein the tubular member comprises a substantially cylindrical core area and an end portion that flares outwardly from the core area such that each portion of the end portion defines a diameter that is greater than a maximum diameter defined by the core area, wherein the core area and the end portion are formed from a single piece of material; and
a helical stabilization member defined about at least a portion of the tubular member such that the core area comprises at least a portion of the stabilization member and the end portion comprises at least a portion of the stabilization member, wherein the stabilization member is configured to reduce the incidence of infolding of the tubular member, wherein the stabilization member has a wall thickness that is less than a wall thickness of the tubular member, wherein, within the core area, the stabilization member extends inwardly within the tubular member to define both an inner diameter and an outer diameter that are less than an inner diameter of the tubular member, and wherein the stabilization member is bounded by transition regions between the tubular member and the stabilization member, the transition regions comprising a bevel.

20. The stent according to claim 19, wherein a depth of the stabilization member is no greater than 10 percent of an outer diameter of the tubular member.

21. The flexible stent according to claim 19, wherein the tubular member further comprises a second end portion that flares outwardly from the core area, and wherein an additional stabilization member comprises a turn defined by a helical groove that extends from the second end portion to the core area.

22. The flexible stent according to claim 19, wherein a longitudinal length of the core area is greater than a longitudinal length of the end portion.

23. A flexible stent configured to be positioned within a lumen proximate to a target area, the flexible stent comprising:
a tubular member that defines at least a portion of each of a proximal end portion, a core portion, and a distal end portion, at least a portion of the tubular member comprising a self-expanding material and is configured to self-expand from a contracted position to an expanded position, wherein at least one of the proximal and distal ends of the tubular member comprises a flared portion that flares outwardly from the core portion such that each portion of the flared portion defines a diameter that is greater than a maximum diameter defined by the core portion, wherein the core portion and the flared portion are formed from a single piece of material; and a plurality of helical stabilization members defined about at least the core portion of the tubular member, each stabilization member extending inwardly within the tubular member to define an inner diameter that is less than an inner diameter of the tubular member within the core portion, the stabilization members being configured to inhibit infolding of the tubular member, wherein portions of the tubular member that are between the stabilization members within the core portion are substantially cylindrical so as not to define a curvature in a longitudinal direction defined by the stent, and wherein the tubular member and stabilization members are integrally formed from a single piece of material, wherein each of the stabilization members is bounded by transition regions between the tubular member and each of the stabilization members, the transition regions comprising a bevel, and wherein at least one stabilization member extends from the core portion into the flared portion.

24. The stent according to claim 23, wherein the plurality of stabilization members comprises a helical groove that has from two to four turns.

* * * * *